United States Patent [19]

Brown et al.

[11] Patent Number: 5,607,566
[45] Date of Patent: Mar. 4, 1997

[54] BATCH DEPOSITION OF POLYMERIC ION SENSOR MEMBRANES

[75] Inventors: Richard B. Brown, Ann Arbor, Mich.; Guen-Sig Cha, Seoul, Rep. of Korea; Howard D. Goldberg, Ann Arbor, Mich.

[73] Assignee: The Board of Regents of the University of Michigan, Ann Arbor, Mich.

[21] Appl. No.: 196,105

[22] PCT Filed: Aug. 20, 1992

[86] PCT No.: PCT/US92/07037

§ 371 Date: Oct. 3, 1994

§ 102(e) Date: Oct. 3, 1994

Related U.S. Application Data

[63] Continuation-in-part of Ser. No. 748,742, Aug. 20, 1991, abandoned, which is a continuation-in-part of Ser. No. 370,897, Jun. 23, 1989, abandoned, Ser. No. 517,636, May 2, 1990, Pat. No. 5,102,526, and Ser. No. 517,651, May 2, 1990, abandoned.

[51] Int. Cl.$^6$ .................................................. G01N 27/26
[52] U.S. Cl. .................... 204/418; 204/403; 204/416; 204/413; 252/62.2; 252/500; 427/282
[58] Field of Search ...................... 204/403, 416, 204/418, 413; 252/62.2, 500; 427/282

[56] References Cited

U.S. PATENT DOCUMENTS

| | | | |
|---|---|---|---|
| 4,454,007 | 6/1984 | Pace | 204/418 |
| 4,670,490 | 6/1987 | Yoshida et al. | 524/115 |

*Primary Examiner*—Bruce F. Bell
*Attorney, Agent, or Firm*—Rohm & Monsanto

[57] ABSTRACT

Screen printing technology is employed in the batch fabrication of the contacts and polymeric membranes of solid-state ion-selective sensors. The process achieves high yield with very reproducible results. Moreover, membrane thickness can easily be predetermined, as it is directly related to the thickness of the screen or stencil. The process of the present invention is compatible with many integrated circuit manufacturing technologies, including CMOS fabrication. Advantageous polymeric membrane paste compositions include a polyurethane/hydroxylated poly(vinyl chloride) compound and a silicone-based compound in appropriate solvent systems to provide screen-printable pastes of the appropriate viscosity and thixotropy.

14 Claims, 3 Drawing Sheets

BATCH DEPOSITION OF POLYMERIC ION SENSOR MEMBRANES

RELATIONSHIP TO OTHER APPLICATIONS

This is a 371 of PCT/US Ser. No. 92/07037 filed Aug. 20, 1992, and a continuation-in-part patent application of U.S. Ser. No. 748,742 filed on Aug. 20, 1991 now abandoned as a continuation-in-part of U.S. Ser. Nos. 370,897, filed Jun. 23, 1989, now abandoned; 517,636, filed May 2, 1990; and 517,651, also filed May 2, 1990, now abandoned. U.S. Ser. No. 517,636 issued as U.S. Pat. No. 5,102,526 on Apr. 7, 1992. The remainder of the aforementioned patent applications are pending at the time of filing the present application, were filed in the names of Richard B. Brown and Geun-Sig Cha, both of whom are inventors herein, and all such applications are assigned to the same assignee as herein. The disclosures of all of said aforementioned patent applications are incorporated herein by reference.

BACKGROUND OF THE INVENTION

This invention relates generally to systems for producing ion sensors, and more particularly, to a system which produces ion sensors which employ ion-responsive membranes formed of polymeric materials using screen printing procedures to achieve high reproducibility.

In order for an ion sensor to be commercially acceptable and successful, it must be possessed of qualities beyond electrochemical performance. In order for a sensor to be cost effective, it must be reproducible using mass production systems. Moreover, there must be common electrochemical response characteristics within the members of a batch fabricated group. If the sensors are not all substantially identical, they will each be characterized by different lifetimes and response characteristics, creating difficulties in the field, not the least of which is the added cost associated with recalibration of equipment whenever the sensor is changed. In general, polymeric membranes are in common use as transducers in solid-state chemical sensors, particularly because such membranes have high selectivity to the ion of interest and can be made selective to a wide range of ions using one or many readily available ionophores. One known technique for forming the membranes is solvent casting; a technique which originated with ion-selective electrode technology. In this approach, the membranes are cast by dissolving their components in an organic solvent, hand depositing the solution onto the sensor sites, and allowing the solvent to be removed by evaporation. In addition to being a rather tedious operation, particularly in view of the small size of the sensors, this production method yields very high losses. The thickness and shape of the membrane cannot be controlled, resulting in an unacceptable lack of sensor reproducibility.

These problems and concerns have been addressed in the prior art, but adequate solutions have not been found. For example, one known approach involves the use of a blank membrane solution to form a coating which conforms to the sensor. The membrane coating is then selectively doped over the multiple sensor sites. This technique suffers from the disadvantage that considerable hand work must be performed under a microscope. In addition, the ionophore will diffuse laterally over time. Moreover, electrical interference in the form of cross-talk through the membrane would limit the geometries and spacings between input pads to dimensions which are unacceptable for multisensing devices.

A further known system employs a lift-off method for patterning permselective membranes. This system requires the patterning of the silicon wafer with a positive photoresist, which results in the photoresist being removed in the areas where the membrane is to be deposited. The dissolved membrane solution is spin coated onto the wafer and allowed to dry. The wafer is immersed in an ultrasonic solvent bath which removes the membrane-coated photoresist regions, resulting in a precisely patterned wafer. This method suffers from the disadvantage of exposing the membranes to organic lift-off solvents which may alter the electrochemical characteristics of the membranes. In addition, the range of thicknesses is limited to those which can be realized in photoresist. Moreover, in multisensing devices, cross-contamination in the ultrasonic lift-off bath can be a problem.

There is not currently available any suitable system for batch fabrication of solid-state ion-selective sensors which employ polymeric membranes. Such membranes can be formed of a variety of polymeric materials, such as poly(vinyl chloride), polyurethane, and silicone.

The use of polyurethane and silicone in the ion-selective membranes of chemical sensors is described in the parent applications enumerated hereinabove. These applications are all incorporated herein by reference.

It is, therefore, an object of this invention to provide a simple and economical system for batch fabrication of solid-state ion-selective sensors.

It is another object of this invention to provide a system for mass producing solid-state ion-selective sensors which employ ion-selective membranes formed of polymeric materials.

It is also an object of this invention to provide a system for batch fabrication of solid-state ion-selective sensors which results in high yield and with high uniformity between the respective sensors.

It is a further object of this invention to provide a substance-sensitive membrane system for a solid-state sensor which can be applied to a plurality of solid-state devices simultaneously using conventional techniques.

It is additionally an object of this invention to provide a substance-sensitive polymeric membrane system for a solid-state sensor which can be applied to a multiplicity of solid-state devices simultaneously using conventional integrated circuit manufacturing techniques.

It is yet a further object of this invention to provide a substance-sensitive membrane for use with a solid-state sensor which does not require a structural layer associated therewith to maintain communication between the membrane and a solid-state substrate.

SUMMARY OF THE INVENTION

The foregoing and other objects are achieved by this invention which provides a method of batch fabricating ion-selective sensors. In accordance with the invention, the method comprises the steps of:
installing a mask on a semiconductor substrate, said mask having at least one aperture therethrough having a predetermined configuration which corresponds with a desired membrane configuration;
applying a polymeric membrane paste to said mask; and
drawing a squeegee across said mask whereby said polymeric membrane paste is urged into said aperture of said mask and into communication with said semiconductor substrate.

In one embodiment of the invention, the mask is formed of a metallic material, which may be a stainless steel mesh. Further, in accordance with the method aspect of the invention, the stainless steel mesh is coated with a photoreactive emulsion.

In a further embodiment, the mask is formed of a metal foil stencil. The membrane which ultimately is produced has a thickness which corresponds to that of the mask. In practical embodiments of the invention, such a thickness may be between 25/μm and 250 μm.

As previously stated, the membrane is formed of a polymeric membrane paste. Such a paste may be formed of a polyurethane with an effective portion of an hydroxylated poly(vinyl chloride) copolymer therein as described in U.S. Ser. No. 517,651; a polyimide-based compound as described in U.S. Ser. No. 746,134; a silicone-based compound, such as silanol-terminated polydimethylsiloxane with the resistance-reducing additive, CN-derivatized silicone rubber described in U.S. Pat. No. 5,102,526; or any other suitable polymeric material.

In a further method step, the screen printed polymeric membrane material is cured after the mask is removed.

In accordance with a product-by-process aspect of the invention, a solid-state ion-selective sensor formed by the process of:

installing a metallic mask on a semiconductor substrate on which are simultaneously formed a plurality of ion-selective sensors, the mask having a pattern formed of a plurality of apertures therethrough, each such aperture having a predetermined configuration which corresponds with a desired membrane configuration for a respectively associated one of the ion-selective sensors;

applying a polymeric membrane paste to the mask; and urging the polymeric membrane paste into the pattern of apertures of the mask and into communication with the semiconductor substrate.

Certain embodiments of the invention include the further step of drawing a squeegee across the mask whereby the polymeric membrane paste is urged into the apertures of the mask and into communication with the semiconductor substrate. In further steps, the mask is removed and the membrane paste is cured.

BRIEF DESCRIPTION OF THE DRAWING

Comprehension of the invention is facilitated by reading the following detailed description, in conjunction with the annexed drawing, in which.

DETAILED DESCRIPTION OF THE INVENTION

Figure 1:
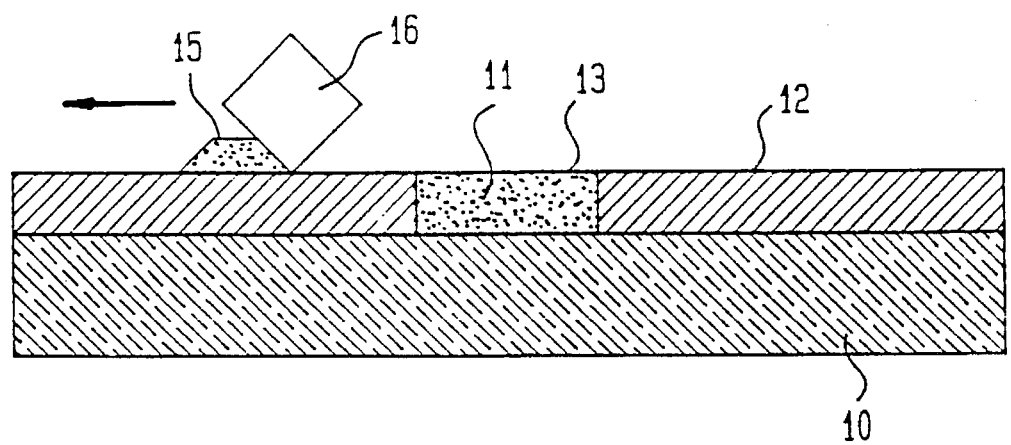
FIG. 1 is a simplified schematic side view which is useful in describing a screen printing process for forming an ion selective membrane.

FIG. 1 is a simplified schematic representation of a silicon wafer upon which is being deposited a polymeric membrane 11. In the practice of the invention, polymeric membrane 11 is ion-selective, as described in the co-pending patent applications which have been incorporated herein.

In the practice of the process of the invention, a mask 12 is installed on silicon wafer 10. The mask has an aperture 13 in which is shown to be deposited the polymeric membrane material. Mask 12 may be formed of a stainless steel mesh coated with a photoreactive emulsion (not shown). Alternatively, the mask may be formed as a metal-foil stencil. In another embodiment, the mask is patterned with the desired features for membrane printing.

A screen printer (not shown) evenly applies the membrane paste, the excess of which is indicated as paste 15, and rubs the paste with a squeegee member 16 which pushes the paste through aperture 13 and onto silicon wafer 10 which functions as a substrate. Squeegee member 16 is, in this embodiment, configured in the shape of a diamond and is moved in the direction of the arrow shown in the figure.

As can be seen from this figure, the thickness of polymeric membrane 11 is responsive to the thickness of mask 12. In practical embodiments of the invention, the mask can have a thickness of approximately between 25 microns and 250 microns. A modem, optical-aligned screen printer, such as model LS-15TV which is commercially available from the New Long Seimitsu Kogyo Company, allows alignment and reproducibility to approximately ±5 microns.

The print quality of the deposited material is a function of mask clearance from the substrate, squeegee speed, squeegee shape, squeegee angle, squeegee pressure, and squeegee push-in quantity. Edge quality of the pattern is determined by squeegee shape and mask clearance from the substrate. Pattern flow-out and thickness is determined primarily by squeegee speed, pressure, and push-in quantity. If squeegee speed is too fast, or is accomplished without enough pressure or push-in quantity, the pattern may not be completely filled with paste, and the deposited material may have peaks, rather than a smooth profile. If the squeegee speed is too slow, or the pressure and push-in quantifies too great, the pattern flow-out will increase and thickness will be decreased due the scavenging effects of the squeegee.

After the membrane paste is applied to the silicon wafer, it must be cured, illustratively, by drying in the air or in an oven at elevated temperatures. Curing conditions are within the skill of a person of ordinary skill in the art. However, we have found that curing should be controlled to avoid evaporation of the membrane components, specifically a plasticizer, if included.

The screen printing method of fabricating solid-state ion-selective sensors of the present invention imposes rheological constraints upon the membrane material. Solvents and additives are used to form the membrane paste, such as paste 15, having an appropriate viscosity and thixotropy to achieve good pattern definition. Viscosity must be adjusted to achieve the appropriate resistance to flow from squeegee motion and thixotropy must be adjusted for appropriate resistance to secondary flow after the mask is removed from the substrate.

For example, anhydrous tetrahydrofuran (THF), which is typically used for solvent cast membranes, is an unacceptable solvent for a screen printing paste due to its high evaporation rate which causes the viscosity of the paste to change rapidly, resulting in clogging of the mask. Other commonly used solvents with lower evaporation rates (i.e., higher boiling points), such as N,N-dimethylacetamide (DMA) and cyclohexanone, or combinations of these solvents and THF, have been tried, but yielded less than satisfactory results. However, in certain embodiments, we have found that THF in the solvent system advantageously facilitates dissolution of the membrane components. THF can be removed from the membrane paste prior to use, for example, by permitting evaporation in a vacuum desiccator.

Use of too little solvent results in a tacky, stringy paste that gels on the mask whereas use of too much solvent results in thinner membranes with poorer pattern definition. The screen printing process itself exacerbates the problem as it continuously spreads a thin layer of paste onto the screen mask thereby increasing the surface area of the membrane paste exposed to air and increasing the solvent evaporation rate.

Another unsuccessful technique used to increase viscosity was the addition of silica powder to the paste composition. The addition of silica powder resulted in poor printability of the membrane paste and membranes with pinholes and other defects. Described hereinbelow are several specific illustrative examples of membrane components and solvent systems used for screen printing good quality ion-selective membranes in accordance with the present invention.

EXAMPLE 1

Polyurethane-based Membrane Paste
26.4 wt. % polyurethane (PU; SG-80A, Tecoflex, Thermedics, Inc., Woburn, Mass.)
6.6 wt. % hydroxylated PVC (PVC/Ac/Hydroxy Propyl Acrylate, 80/5/15 wt. %) Scientific Polymer Products, Ontario, N.Y.)
66 wt. % plasticizer (bis(2-ethylhexyl)adipate, Fluka, Ronkonkoma, N.Y.)
1 wt. % ionophore (e.g., valinomycin or nonactin)

In one illustrative example, the membrane components were completely dissolved in THF. The high boiling point solvent, 1-methyl-2-pyrrolidinone was added to the solution and thoroughly mixed. Then, the THF was removed in a vacuum desiccator. A membrane paste with good viscosity and screen printability was achieved.

In a preferred embodiment of the invention, PI-Thinner, a proprietary mixture of various high-boiling point solvents, available from Epoxy Technology, Billerica, Mass. was used in the solvent system. In an illustrative method embodiment, the membrane components were dissolved in 1.2 ml THF. Then, 0.1 ml PI-Thinner were added and allowed to mix thoroughly. HF was evaporated from the resulting membrane paste.

In some embodiments of the invention, a silanating agent or adhesion promotor, silicon tetrachloride ($SiCl_4$), was added to the paste prior to printing in order to increase membrane adhesion to the semiconductor surface and to improve the resulting electrode stability. In the preferred embodiment described immediately hereinabove, $SiCl_4$ (7 wt. %) was added just prior to printing.

An illustrative cure cycle for the preferred embodiment consists of a 1 hour convection oven bake (70° C.) to accelerate the PI-Thinner evaporation process, followed by a room temperature cure for approximately 24 hours.

Of course, other plasticizers, ionophores, or fillers known in the art may be used in the illustrative membrane compositions set forth herein without departing from the principles of the invention.

EXAMPLE 2

Silicone Rubber Membrane Paste
A moisture-curable silicone rubber-based formulation comprises:
97.2 wt. % silicone rubber (RTV 3140; Dow Coming, Midland, Mich.)
1.0 wt. % lipophilic additive, e.g., potassium tetrakis(p-chlorophenyl)borate (Fluka, Ronkonkoma, N.Y.)
1.8 wt. % ionophore The membrane components were completely dissolved in 1.2 ml THF. The THF was evaporated and the resulting paste is ready for screen printing. No adhesion promoting agent, such as $SiCl_4$, is necessary or desirable in this composition. The resulting membranes can be cured at room temperature for 24 hours in the ambient atmosphere to allow the vulcanizing process to occur.

EXAMPLE 3

Figure 2:
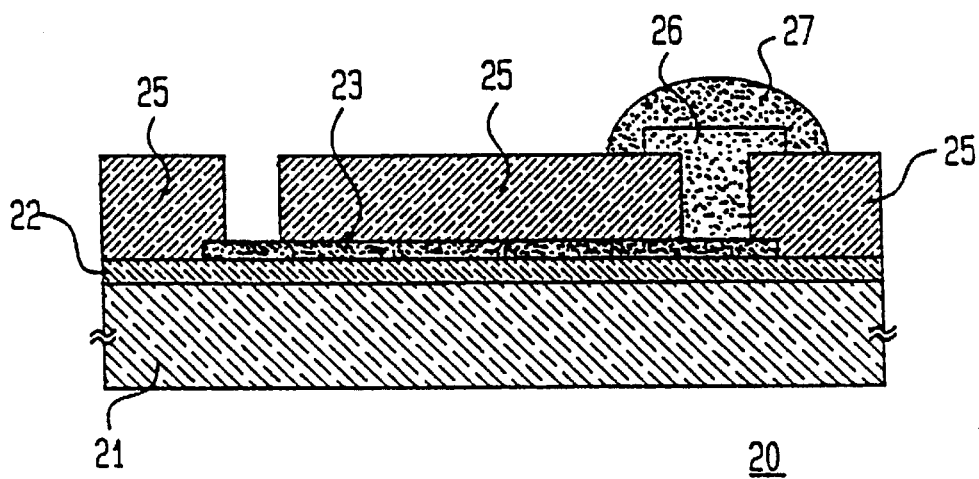
FIG. 2 is a simplified schematic representation of a solid-state microelectrode constructed in accordance with the invention.

Screen-Printed Solid-State Ion-Selective Electrodes
FIG. 2 is a simplified schematic representation of a solid-state microelectrode 20 which was fabricated using the screen printing system of the present invention with CMOS-compatible technology. Solid-state microelectrode 20 is shown to have a silicon substrate 21 with a layer of silicon dioxide 22 thereon. An aluminum electrode 23 is deposited on the silicon dioxide layer and a layer of silicon nitride 25 is arranged over the aluminum electrode and the silicon dioxide layer. A screen printing process similar to that described hereinabove with respect to FIG. 1 was employed to produce a silver epoxy contact 26. The epoxy may be of the type which is commercially available. In addition, a polymeric membrane 27 was also produced using the screen printing process and arranged to overlie the solid silver epoxy contact. Thus, screen printing technology is applicable to the fabrication of the contacts and the membranes.

It is highly desirable that the ion-selective membranes, such as the polyurethane-based membrane described in Example 1, be of a type which adheres well to silicon-based materials, such as silicon nitride layer 25. Such adhesion reduces the probability that electrolyte shunts will form behind the membrane, rendering the solid-state microelectrode inoperative.

In a specific illustrative embodiment, the sensor dimensions shown in FIG. 2 are 1.5 cm by 1.0 cm and the silicon nitride via hole it the electrode site is 600 $\mu m^2$. Stainless steel stencil masks (Micro-Screen, South Bend, Ind. were used to print silver epoxy electrode contacts (Epotek H20E; Epoxy Technology, Billeries, Mass.) and the polymer membranes on solid-state sensors. The silver epoxy contact is ideally 660 $\mu m$ on a side and 102 $\mu m$ thick. The silver epoxy contact was deposited by screen printing Epotek H20E and curing for 15 minutes in a 150° C. oven.

Table 1 shows the screen printing parameters used to print the silver and polymeric sensor layers in the device of FIG. 2. The polymeric sensor layers comprise membrane paste as prepared in the preferred embodiment of Example 1 (PU/PVC/Ac/Al) and Example 2 (silicone rubber). The parameters may be adjusted from run-to-run to compensate for slight variations in the rheology of the membrane paste.

TABLE 1

| Parameter | Silver Epoxy | PU/(PVC/Ac/Al) | Silicone Rubber |
|---|---|---|---|
| mask clearance | 0 mm | 0 mm | 0 mm |
| squeegee shape | diamond | square edge | square edge |
| squeegee speed | 100 mm/sec | 100 mm/sec | 150 mm/sec |
| squeegee angle | none | 60° | 60° |
| squeegee pressure | 0.9 kg/cm$^2$ | 1.0 kg/cm$^2$ | 1.1 kg/cm$^2$ |
| push-in quantity | 0.1 mm | 0.1 mm | 0 mm |

The pattern definition quality of the respective screen printed layers is summarized in Table 2. Lateral flow-out was determined by an automatic surface profiler (Sloan DekTak II) and film thickness was determined by a scanning electron microscope image of a cleaved sample.

TABLE 2

| Quality | Silver Epoxy | PU/(PVC/Ac/Al) | Silicone Rubber |
|---|---|---|---|
| mask thickness (± 12.7 μm) | 76 μm | 127 μm | 127 μm |
| layer thickness | 40 μm | 83 μm | 127 μm |
| lateral flow-out | 25 ± 16 μm | 66 ± 12 μm | 48 ± 10 μm |

EXAMPLE 4

Ammonium Ion Sensing Electrodes

Using the compositions of Examples 1 and 2 as the printing paste, electrodes were fabricated in accordance with the method and parameters set forth hereinabove in Example 3. Nonactin (Fluka, Ronkonkoma, N.Y.) was used as the ionophore in the formulation to create an ammonium ion sensitive electrode.

Figure 3:
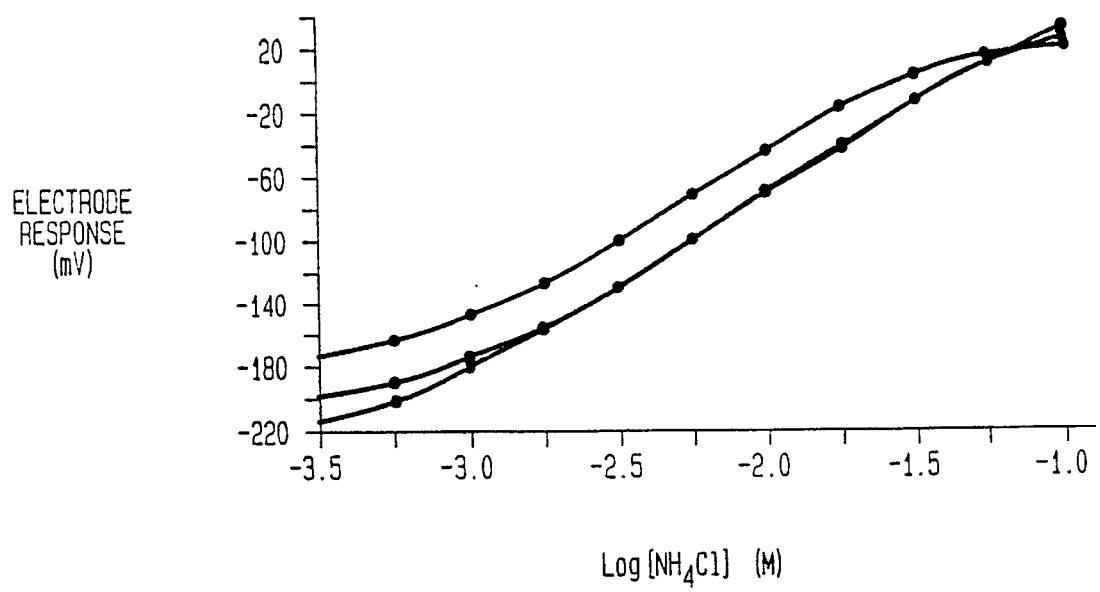
FIG. 3 is a graphical representation of the ammonium ion response of screen printed polyurethane-based membranes of the present invention plotted as a function of electrode response in mV against the log of the ammonium ion concentration in moles over the concentration range $10^{-3}$ to $10^{-1.5}$ M.
Figure 4:
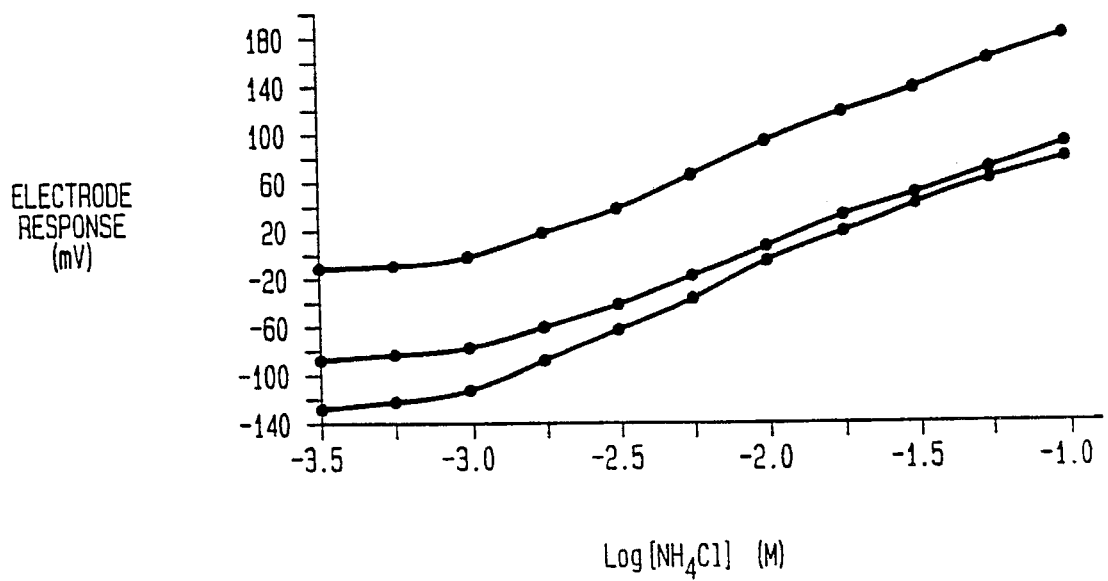
FIG. 4 is a graphical representation of the ammonium ion response of screen printed silicone rubber-based membranes of the present invention plotted as a function of electrode response in mV against the log of the ammonium ion concentration in moles over the concentration range $10^{-3}$ to $10^{-1.5}$ M.

Using a sleeve-type double junction Ag/AgCl electrode (Orion, Model 90-02) as the external reference electrode, calibration curves plots obtained by taking emf measurements every 10 seconds from additions of standard solutions of ammonium chloride in 250 ml background electrolyte (0.05 mol/L Tris-HCl, pH 7.2) at room temperature. FIGS. 3 and 4 show the ammonium ion response of the screen printed ion-selective membranes of the present invention. Referring to FIG. 3, the average slope for the 3 sensors tested with the PU/PVC/Ac/Al) membrane is 51.4 mV/decade over the concentration range $10^{-3}$ to $10^{-1.5}$ M. Referring to FIG. 4, the average slope for the 3 sensors with the silicone rubber membrane is 48.9 mV/decade. The sensors were soaked in Tris-HCl buffer (pH 7.2), at room temperature, between measurements. The response of the sensors was measured each day for a 33 day period and found to be quite stable.

EXAMPLE 5

Multisensor Chip

Figure 5:
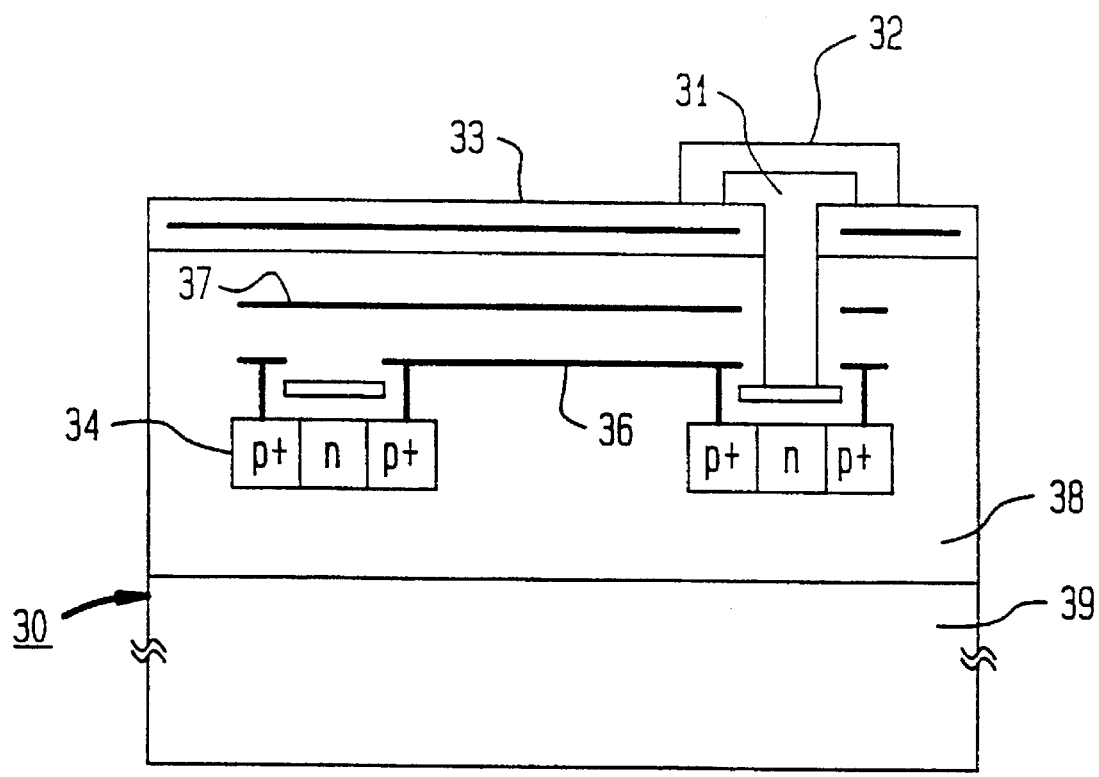
FIG. 5 is a schematic cross-section of a single electrode site on a multisensor.

FIG. 5 is a schematic cross-section of a single electrode site on a multisensor chip 30. More specifically, the circuitry is realized by a 2 μm double-metal double-polysilicon p-well process using silicon-on-insulator (SOI) wafers. An ion-selective electrode has silver epoxy contact 31, which connects directly to an SOI transistor 34 of an operational amplifier buffer below it. Contact 31 is coated with a polymer membrane 32 which additionally communicates with a silicon nitride layer 33. A first metal layer 36 is coupled to SOI transistor 34. A second metal layer 37 functions as a ground shield in this embodiment to prevent long-term encapsulation layer breakdown. The SOI transistor and the first and second metal layers are arranged in a layer 38 of silicon dioxide, which is itself deposited on a silicon substrate 39. Thus, in this embodiment, there is achieved three-dimensional dielectric encapsulation of all circuit nodes from the test solution. The sensor-specific layers were post-deposited on the microelectronics using the screen printing techniques of the present invention.

The screen printing techniques of the present invention can be used to devise a wide variety of solid-state sensors and actuators. For example, biosensors can be formed by the screen printing techniques described herein, by printing asymmetrical (multilayer) membranes or bioreactive reagents suspended in gels over the sensor sites. Various combinations of ion- and bio-selective electrode sites could be realized on a monolithic chip containing appropriate microelectronics.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A method of batch fabricating ion-selective sensors, the method comprising the steps of:

installing a mask on a semiconductor substrate, the mask having at least one aperture therethrough having a set configuration which corresponds to a chosen membrane configuration;

applying a polymeric membrane paste to the mask, the polymeric membrane being in the form of a mixture of a polyurethane polymer, hydroxylated poly(vinyl chloride) copolymer, ionophore, and a plasticizer, as polymeric membrane components dissolved completely in a second solvent after a first solvent has been removed from the polymeric membrane paste;

drawing a squeegee across said mask wherein the polymeric membrane paste is urged into the aperture of the mask and into communication with the semiconductor substrate; and curing the deposited polymeric membrane paste to form a polymeric membrane having a set ion-selective characteristic.

2. The method of claim 1 wherein said mask is formed of a metallic material.

3. The method of claim 2 wherein the mask is formed of a stainless steel mesh and there is further provided the step of coating the stainless steel mesh with a photoreactive emulsion.

4. The method of claim 2 wherein the mask is formed of a metal-foil stencil.

5. A method of batch fabricating ion-selective sensors, the method comprising the steps of:

installing a metallic mask on a semiconductor substrate on which are simultaneously formed a plurality of the ion-selective sensors, the mask being patterned to have a plurality of apertures therethrough, each having a set configuration which corresponds to a chosen membrane configuration, and each being located as to be associated with one of the ion-selective sensors;

applying a polymeric membrane paste to the mask, the polymeric membrane being in the form of a mixture of a polyurethane polymer, hydroxylated poly(vinyl chloride) copolymer, ionophore, and a plasticizer, as polymeric membrane components dissolved completely in a second solvent after a first solvent has been removed from the polymeric membrane paste;

urging the polymeric membrane paste into the pattern of apertures of the mask and into communication with the semiconductor substrate; and curing the deposited polymeric membrane paste to form a polymeric membrane having a set ion-selective characteristic.

6. The method of claim 5 wherein the step of urging comprises drawing a squeegee across the mask at a set distance from the mask with a set squeegee speed, squeegee shape, squeegee angle, squeegee pressure, and squeegee push-in quantity.

7. A solid-state ion-selective sensor formed by the process of:

installing a metallic mask on a semiconductor substrate on which are simultaneously formed a plurality of ion-selective sensors, the mask having a pattern formed of a plurality of apertures therethrough, each such aperture having a set configuration which corresponds to a chosen membrane configuration for a respectively associated one of the ion-selective sensors;

applying a polymeric membrane paste to the mask, the polymeric membrane being in the form of a mixture of a polyurethane polymer, hydroxylated poly(vinyl chloride) copolymer, ionophore, and a plasticizer, as polymeric membrane components dissolved completely in a second solvent after a first solvent has been removed from the polymeric membrane paste;

urging the polymeric membrane paste into the pattern of apertures of the mask and into communication with the semiconductor substrate; and curing the deposited polymeric membrane paste to form a polymeric membrane having a set ion-selective characteristic.

8. The solid state ion-selective sensor of claim 7 wherein the step of urging comprises drawing a squeegee across the mask at a set distance from the mask with a set squeegee speed, squeegee shape, squeegee angle, squeegee pressure, and squeegee push-in quantity.

9. A process for forming a polymeric membrane paste, the process comprising the steps of:

mixing polyurethane, hydroxylated poly(vinyl chloride) copolymer ionophore, and a plasticizer, as polymeric membrane components, in a first solvent have a first boiling point in order to dissolve completely the components;

adding a second solvent having a second boiling point higher than the first boiling point; and removing the first solvent.

10. The process of claim 9 further comprising the step of adding an adhesion promotor after the step of removing the first solvent.

11. The process of claim 9 wherein the step of mixing further includes adding an ionophore.

12. A process for forming a polymeric membrane paste, the process comprising the steps of:

mixing silicone rubber and a lipophilic additive in a solvent in order to completely dissolve the components; and evaporating the solvent.

13. The process of claim 12 wherein the polymeric membrane components comprise silicone rubber and a lipophilic additive.

14. The process of claim 12 wherein the step of mixing further includes adding an ionophore.

* * * * *